US010642954B2

(12) United States Patent
Baumgart et al.

(10) Patent No.: US 10,642,954 B2
(45) Date of Patent: May 5, 2020

(54) MEDICAL SCANNER OPTIMIZED WORKFLOW SYSTEM (71) Applicant: Siemens Medical Solutions USA, Inc., Malvern, PA (US)

(72) Inventors: John Baumgart, Hoffman Estates, IL (US); Soroosh Kargar, Lake in the Hills, IL (US); Priyendu Subashchandran, Schaumburg, IL (US); Abdul Salim Vahabudeen, Algonquin, IL (US)

(73) Assignee: Siemens Healthcare GmbH, Erlangen (DE)

( * ) Notice: Subject to any disclaimer, the term of this patent is extended or adjusted under 35 U.S.C. 154(b) by 778 days.

(21) Appl. No.: 14/480,825

(22) Filed: Sep. 9, 2014

(65) Prior Publication Data

US 2015/0161340 A1 Jun. 11, 2015

Related U.S. Application Data (60) Provisional application No. 61/913,984, filed on Dec. 10, 2013.

(51) Int. Cl.
*G16H 50/20* (2018.01)
*G06F 3/0484* (2013.01)
(Continued)

(52) U.S. Cl.
CPC .......... *G06F 19/321* (2013.01); *G06F 3/0481* (2013.01); *G06F 3/04842* (2013.01); *G16H 50/20* (2018.01); *G06F 2203/04803* (2013.01)

(58) Field of Classification Search
CPC ........ G06C 50/22; G06C 50/24; G06C 40/08; G06C 10/10; G06F 19/322; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462;
(Continued)

(56) References Cited

U.S. PATENT DOCUMENTS 6,029,138 A * 2/2000 Khorasani ............ G06F 19/324
600/300
6,603,494 B1 * 8/2003 Banks ..................... A61B 5/411
600/410

(Continued)

*Primary Examiner* — Eliza A Lam (57) ABSTRACT

A medical workflow system is provided that includes at least one database configured to store one or more programs that operate a patient imaging device, patient data corresponding to one or more patients, medical procedure data corresponding to a type of patient medical procedure, and user data identifying a user to conduct a medical procedure using the medical procedure data. The medical workflow system includes a workflow processor configured to determine which of the one or more programs to provide to the user based on at least one of the patient data, the medical procedure data and the user data. The medical workflow system also includes at least one user interface configured to provide a plurality of user selectable options comprising the determined one or more or programs. The workflow processor is further configured to execute a selected program that is selected from the one or more provided programs.

22 Claims, 6 Drawing Sheets

(51) Int. Cl.
    *G06F 3/0481*         (2013.01)
    *G06F 19/00*          (2018.01)

(58) Field of Classification Search
    CPC ............. G06F 19/3468; G06F 19/3475; G06F 19/3481; G06F 19/36; G06Q 10/10; G06Q 50/22; G06Q 50/24; G06Q 40/08; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/40; G16H 70/60; G16H 80/00
    See application file for complete search history.

(56) References Cited

U.S. PATENT DOCUMENTS 8,380,533 B2 *   2/2013   Reicher ................. G06Q 10/10
                                                       705/2
2007/0143499 A1 *   6/2007   Chang .................... H04L 67/18
                                                       709/245

* cited by examiner

MEDICAL SCANNER OPTIMIZED WORKFLOW SYSTEM

CROSS-REFERENCE TO RELATED APPLICATIONS

This application claims priority to U.S. provisional application Ser. No. 61/913,984 filed Dec. 10, 2013, which is incorporated herein by reference in its entirety.

TECHNOLOGY FIELD

The present application relates generally to an enhanced medical workflow system and method, and in particular, to methods and systems for minimizing procedure turnaround time in an examination room.

BACKGROUND

Conventional medical workflow associated with medical procedure typically includes multiple steps. These steps may include preparation and planning for a patient and setting up scan program parameters and other variables, such as an angle of a C-arm of the patient imaging device. Performing each task affects the turnaround time of each procedure, thereby impacting the efficiency in the examination room. What is needed is a more efficient medical workflow system and method.

SUMMARY

Embodiments provide a medical workflow system that includes at least one database configured to store one or more programs that operate a patient imaging device, patient data corresponding to one or more patients, medical procedure data corresponding to a type of patient medical procedure, and user data identifying a user to conduct a medical procedure using the medical procedure data. The medical workflow system also includes a workflow processor configured to determine which of the one or more programs to provide to the user based on at least one of the patient data, the medical procedure data and the user data. The medical workflow system further includes at least one user interface configured to provide a plurality of user selectable options comprising the determined one or more or programs. The workflow processor is further configured to execute a selected program that is selected from the one or more provided programs.

According to one embodiment, the plurality of user selectable options include an option to modify the one or more programs and the processor is configured to modify the one or more programs in response to a selection to modify the one or more programs.

According to another embodiment, the plurality of user selectable options include an option to create one or more new programs and the processor is configured to execute the one or more new programs in response to a selection to create the one or more new programs.

In one embodiment, the one or more programs include image acquisition parameters of the patient imaging device.

In an aspect of an embodiment, the acquisition parameters include at least one of a voltage of the patient imaging device or a current of the patient imaging device, or an angulation of a C-arm.

According to one embodiment, the processor is further configured to match the one or more programs with the patient data to determine which of the one or more programs to provide to the user.

According to another embodiment, the processor is further configured to match the one or more programs with the medical procedure data to determine which of the one or more programs to provide to the user.

In one embodiment, the processor is further configured to match the one or more programs with the user data to determine which of the one or more programs to provide to the user.

In yet another embodiment, the user is a physician.

Embodiments provide a medical workflow method that includes storing one or more programs in a database used to operate a patient imaging device and storing, in the database, at least one of: (i) patient data corresponding to one or more patients; (ii) medical procedure data corresponding to a type of patient medical procedure; and (iii) user data identifying a user to conduct a medical procedure using the medical procedure data. The method also includes managing, by a workflow processor, the at least one of: (i) the one or more programs; (ii) the patient data; (iii) the medical procedure data; and (iv) the user data and determining, by the workflow processor, which of the one or more programs to display to the user for user selection via a user interface based on at least one of the patient data, the medical procedure data and the user data. The method further includes providing, via a user interface, a plurality of user selectable options comprising the determined one or more or programs and executing, by the workflow processor, a selected program selected from the one or more provided programs.

According to an embodiment, the method further includes providing, via the user interface, an option to modify the one or more programs and modifying, by the workflow processor, the one or more programs in response to a selection to modify the one or more programs.

According to another embodiment, the method further includes providing, via the user interface, an option to create one or more new programs and executing, by the workflow processor, the one or more new programs in response to a selection to create the one or more new programs.

In one embodiment, the method further includes matching, by the workflow processor, the one or more programs with the patient data to determine which of the one or more programs to provide to the user.

In another embodiment, the method further includes matching, by the workflow processor, the one or more programs with the medical procedure data to determine which of the one or more programs to provide to the user.

According to an embodiment, the method further includes matching, by the workflow processor, the one or more programs with the user data to determine which of the one or more programs to provide to the user.

In yet another embodiment, the method further includes tracking, by the workflow processor, user selection of the one or more programs and labeling the one or more selected programs based on the frequency of use of the program by a user.

Embodiments provide an article of manufacture for operating a workflow management system, the article of manufacture comprising a non-transitory, tangible computer-readable medium holding computer-executable instructions for performing a method that includes storing one or more programs in a database used to operate a patient imaging device and storing, in the database, at least one of: (i) patient data corresponding to one or more patients; (ii) medical procedure data corresponding to a type of patient medical procedure; and (iii) user data identifying a user to conduct a medical procedure using the medical procedure data.

In one embodiment, the medium holds computer-executable instructions for performing the method that also includes managing, by a workflow processor, the at least one of: (i) the one or more programs; (ii) the patient data; (iii) the medical procedure data; and (iv) the user data and determining, by the workflow processor, which of the one or more programs to display to the user for user selection via a user interface based on at least one of the patient data, the medical procedure data and the user data. The method also includes providing, via a user interface, a plurality of user selectable options comprising the determined one or more or programs and executing, by the workflow processor, a selected program selected from the one or more provided programs.

In another embodiment, the medium holds computer-executable instructions for performing the method that also includes providing, via the user interface, an option to modify the one or more programs and modifying, by the workflow processor, the one or more programs in response to a selection to modify the one or more programs.

According to an embodiment, the medium holds computer-executable instructions for performing the method that also includes providing, via the user interface, an option to create one or more new programs and executing, by the workflow processor, the one or more new programs in response to a selection to create the one or more new programs.

According to another embodiment, the medium holds computer-executable instructions for performing the method that also includes matching, by the workflow processor, the one or more programs with at least one of: (i) the patient data; (ii) the medical procedure data; and (iii) the user data to determine which of the one or more programs to provide to the user.

Additional features and advantages of this disclosure will be made apparent from the following detailed description of illustrative embodiments that proceeds with reference to the accompanying drawings.

BRIEF DESCRIPTION OF THE DRAWING

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF EXEMPLARY EMBODIMENTS

Embodiments of the present disclosure provide a more efficient medical workflow system. Embodiments of the present disclosure provide systems and methods that minimize the turnaround time of procedures in examination rooms. Embodiments of the present disclosure reduce the turnaround time of medical procedures that incorporate scanning of a patient.

Embodiments of the present disclosure include a workflow management system that may be used for patient medical examination, such as performing X-ray imaging related procedures. Examples of X-ray imaging related procedures may include interventional vascular X-ray treatment in cardiac, as well as general angiography procedures.

Embodiments include workflow management systems and methods that provide users (e.g., physicians) with access to patient information prior to scheduled medical procedure. Accordingly, users may create a list of programs prior to the medical procedure that may be executed during the medical procedure.

Embodiments include workflow management systems and methods that incorporate a workflow processor to implement and manage one or more executable applications or programs, such as SPO programs. Embodiments may include a workflow management system that uses a plurality of programs including one or more SPO programs. The SPO program may be a collection of the executables and parameters that are used to operate the X-ray imaging and conduct tasks in a medical procedure. SPO programs may include parameters for tasks in handling specific organ procedures. SPO programs may include separate, or in addition to tasks for organ procedures, other parameters such as a C-Arm start position.

In some embodiments, workflow processors may acquire, combine, manage, organize, and/or auto-generate the parameters of one or more SPO programs. Embodiments include workflow processors that preselect parameters for examination, including parameters in addition to those parameters preselected under one or more SPO programs. Examples of these parameters may include acquisition parameters including strength of X-ray such as an amount of voltage or current. Other acquisition parameters may include the angulation of a C-arm (shown in FIG. 1). The angulation may provide for a specific view of an organ of a patient. Embodiments may include workflow processors that interact (e.g., via a user interface (UI) shown in FIG. 1) with a user (e.g., a physician) such that acquisition parameters preselected by the workflow processors may be subsequently tailored to the preferences of the user and/or the demographics of the patient.

Figure 1:
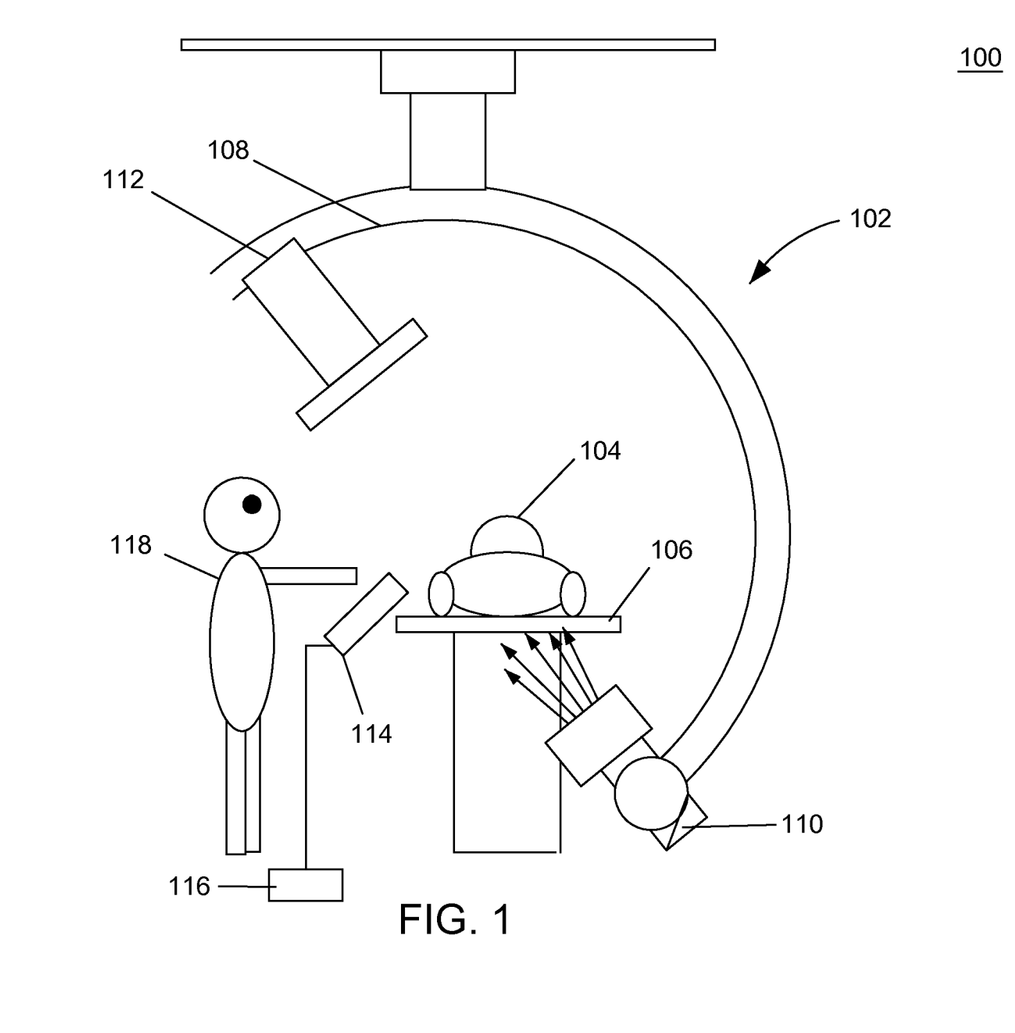
FIG. 1 is an illustration showing an exemplary X-ray examination system for obtaining X-rays of a patient for use with embodiments disclosed herein.

FIG. 1 shows an exemplary X-ray examination system 100 for conducting X-ray imaging of a patient for use with embodiments disclosed herein. X-ray examination system 100 may be located in an examination room of a hospital or other healthcare facility. In some embodiments, the examination room may be a room of a cardiovascular laboratory or interventional angiographic/neurovascular location.

As shown in FIG. 1, system 100 may include an X-ray imaging device 102, and table 106 configured to hold patient 104. The an X-ray imaging device 102 may also be referred to as a scanner, which in some embodiments may include a magnetic resonance (MR) scanner, a computerized tomography (CT) scanner, or ultra-sound device.

Figure 3:
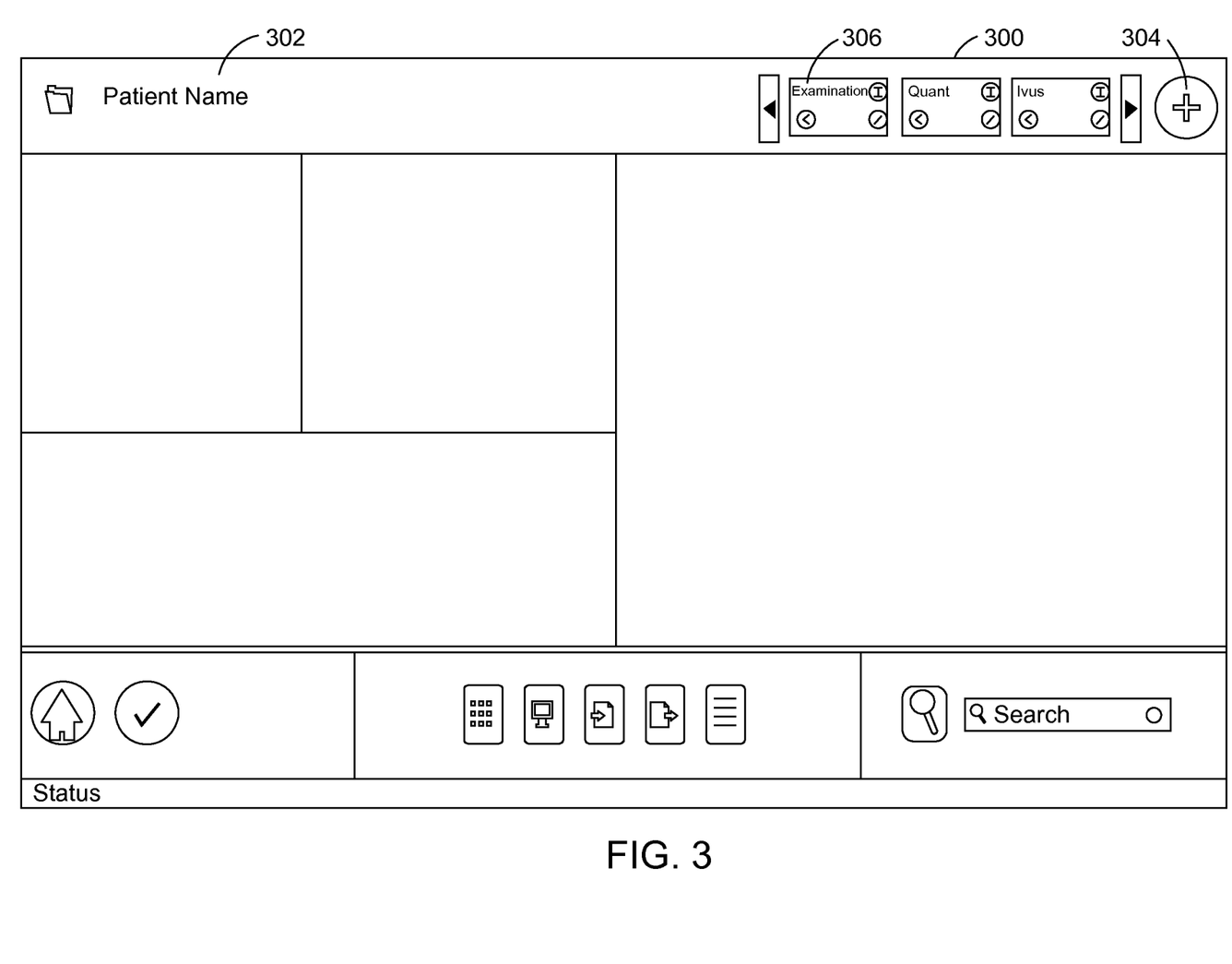
FIG. 3 is an exemplary screen shot showing an SPO program interface according to embodiments described herein.

The X-ray imaging device 102 may include a C-arm 108, an X-ray radiation source 110, an imaging detector 112 and an input device 114 that may display an interface (such as interface 300 shown in FIG. 3). The C-arm 108 may be moved and manipulated around the patient 104. As shown in FIG. 1, the C-arm 108 may support the X-ray radiation source 110 and imaging detector 112 rotating about the patient table 106. The imaging detector 112 detects X-rays provided by the radiation source 110 and passed through the anatomy of patient 104. In some embodiments, the X-ray imaging device 102 may be in the shape of a tube. Embodiments may, however, include imaging devices having other shapes.

In some embodiments, input devices (e.g., input device 114) may be touch panels. In other embodiments, the input devices may be a computer work station having a mouse and keyboard. A user (e.g., physician) 118 may manipulate the C-arm 108 and instruct the X-ray imaging device 102 to capture or acquire images from different angles by using the input device 114. As shown in FIG. 1, the UI 114 may be in communication with a workflow processor 116.

Figure 2:
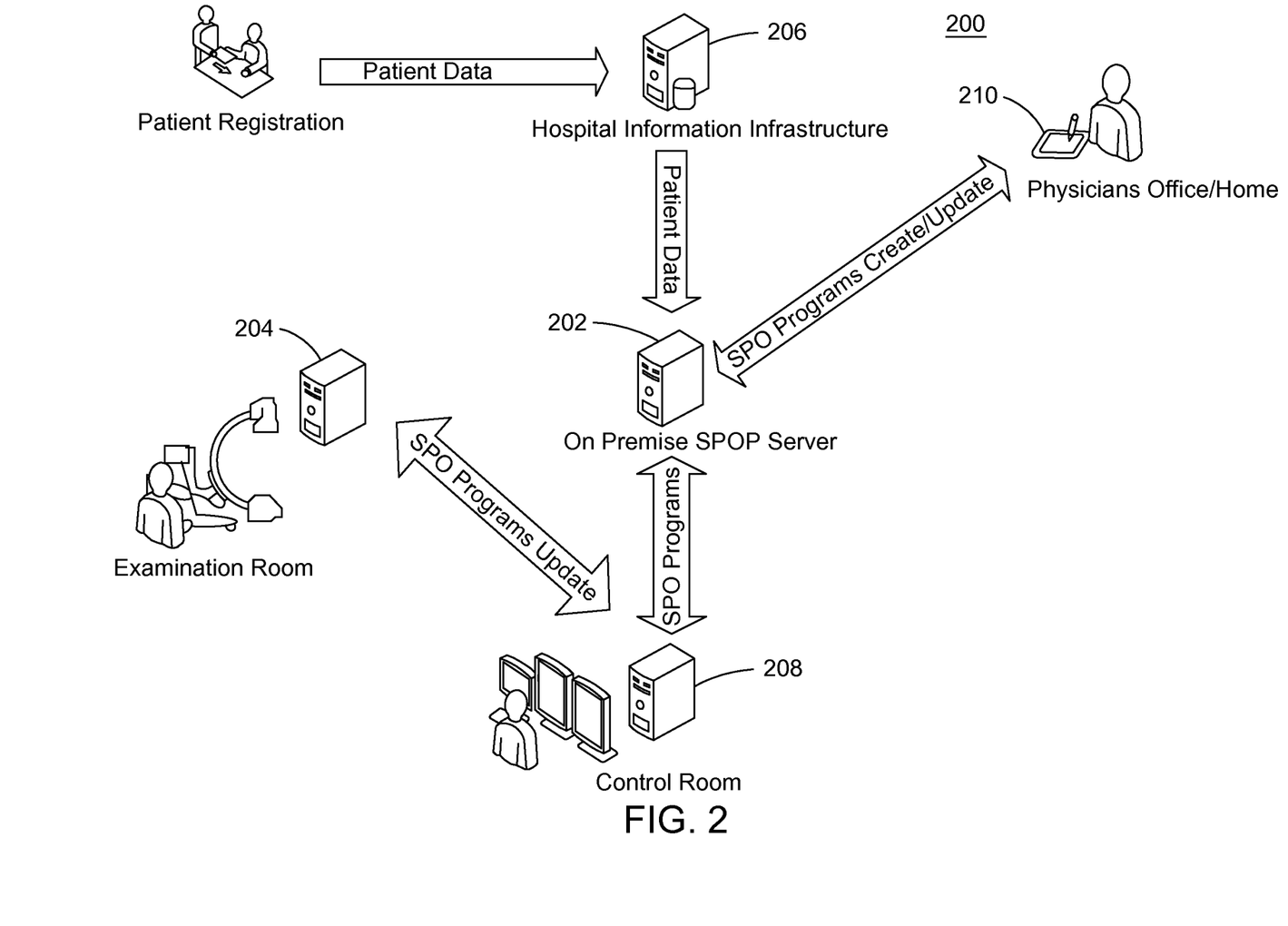
FIG. 2 is a system flow diagram illustrating information routing in an exemplary scan parameter optimized (SPO) program-based medical workflow system according to embodiments described herein.

FIG. 2 is a system flow diagram illustrating information routing in an SPO program based medical workflow system 200 according to embodiments described herein. As shown in FIG. 2, the workflow management system 200 may include one or more computing components configured to acquire, create, modify, and/or utilize information and/or programs prior to and during a medical procedure. These computing components may include SPO program (SPOP) server 202, examination room computer 204, hospital information infrastructure (HII) computer 206, control room computer 208 and physicians computer 210. Embodiments may also include other user computers, such as computers used by a nurse or medical staff member. Embodiments may include workflow systems having any number of computers.

Figure 5:
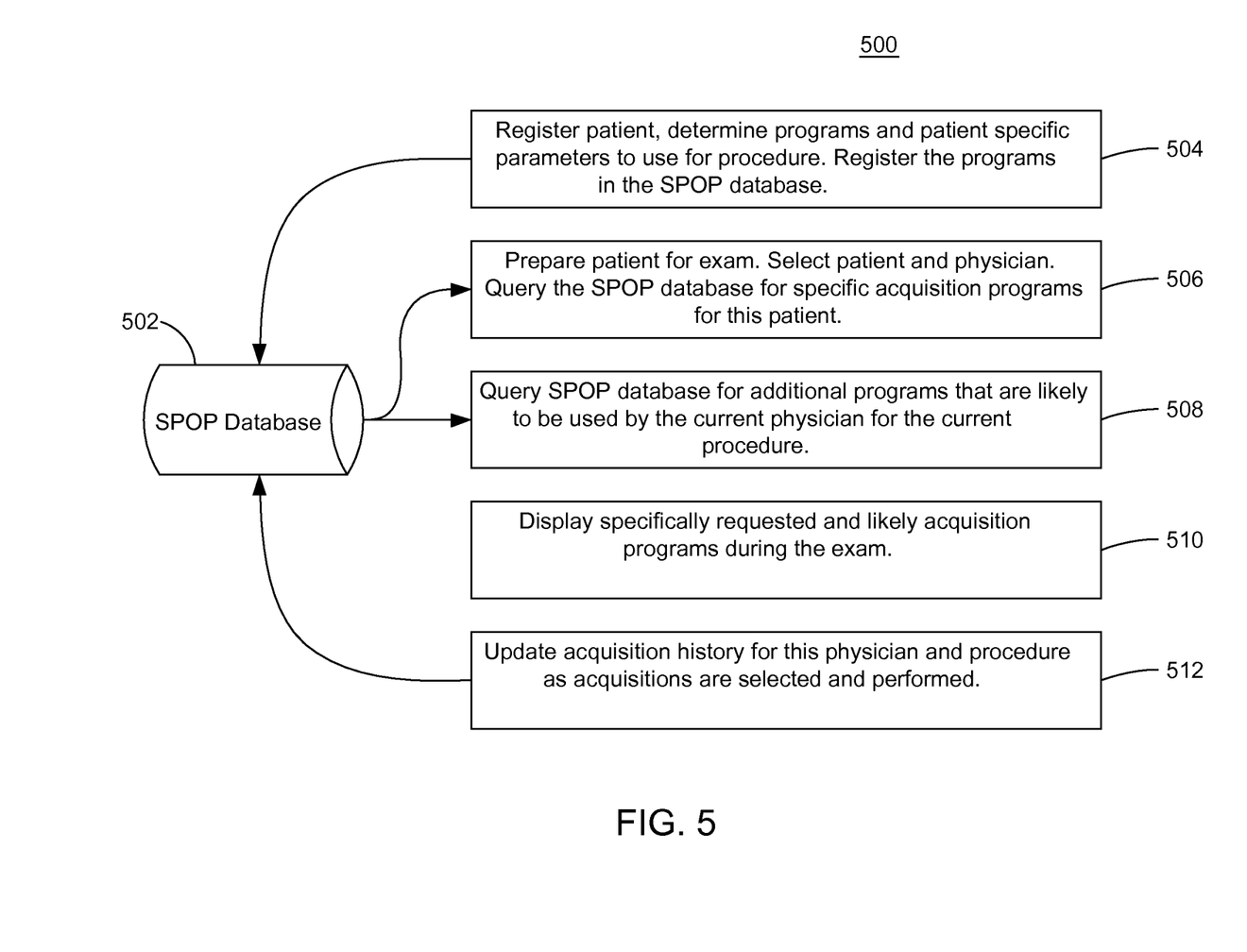
FIG. 5 is a system flow diagram illustrating exemplary workflow and interaction with an SPO program database according to embodiments described herein.

FIG. 5 is a system flow diagram 500 illustrating exemplary workflow and interaction with an SPOP database 502. The SPOP database 502 (shown in FIG. 5) may be partially or fully located within the SPOP server 202 shown in FIG. 2. The workflow processor 116 (shown in FIG. 1) may be located within or in connection with the SPOP server 202. The workflow processor 116 may electronically connect (via wired connection or wireless connection) and communicate with the SPOP database. Alternatively, the workflow processor 116 may be partitioned, with some portion of the processor located in the SPOP server 202 and other partitions located elsewhere, such as in the examination room computer 204, hospital information infrastructure (HII) computer 206 and control room computer 208. The workflow processor 116 may be electrically connected to communicate or wirelessly communicate with examination room computer 204, hospital information infrastructure (HII) computer 206, control room computer 208 and physicians computer 210, and/or other computing devices used by users of the system 200, including physicians.

Referring again to FIG. 2, patient information is first submitted at patient registration and entered as patient information data into the hospital information infrastructure (HII) computer 206. The information is typically entered by healthcare personnel having interviewed the patient, or may be directly entered into a computing terminal by the patient. The hospital information infrastructure (HII) computer 206 may be a single computing device, or multiple computing devices, which may include a server having a database to store patient related information.

When the patient data is available in the hospital information infrastructure (HII) computer 206, the patient data may be automatically transferred (e.g., pushed) to the SPOP server 202 for storage in the SPOP database 502. In some embodiments, the data may be transferred via Health Level Seven (HL7). In other embodiments, data may be transferred via other protocols. The patient data may then be managed by the workflow processor 116, and stored in the SPOP database 502. In other embodiments, the workflow processor 116 may request or independently search and acquire patient data from the hospital information infrastructure (HII) computer 206 or elsewhere. In other embodiments, the SPOP server 202 may be located within a hospital network.

A physician may later request the patient data from the workflow processor 116 which may retrieve the patient data from the SPOP database 502 for delivery to the physician's computing device 210. Examples of the physician's computing devices may include, but not limited to, a tablet, a PC, a smartphone, and a laptop. Physician's computing device may be located at a physician's office, home, or elsewhere. The physician may then commence a process of planning and preparation for a future patient medical procedure.

Figure 4:
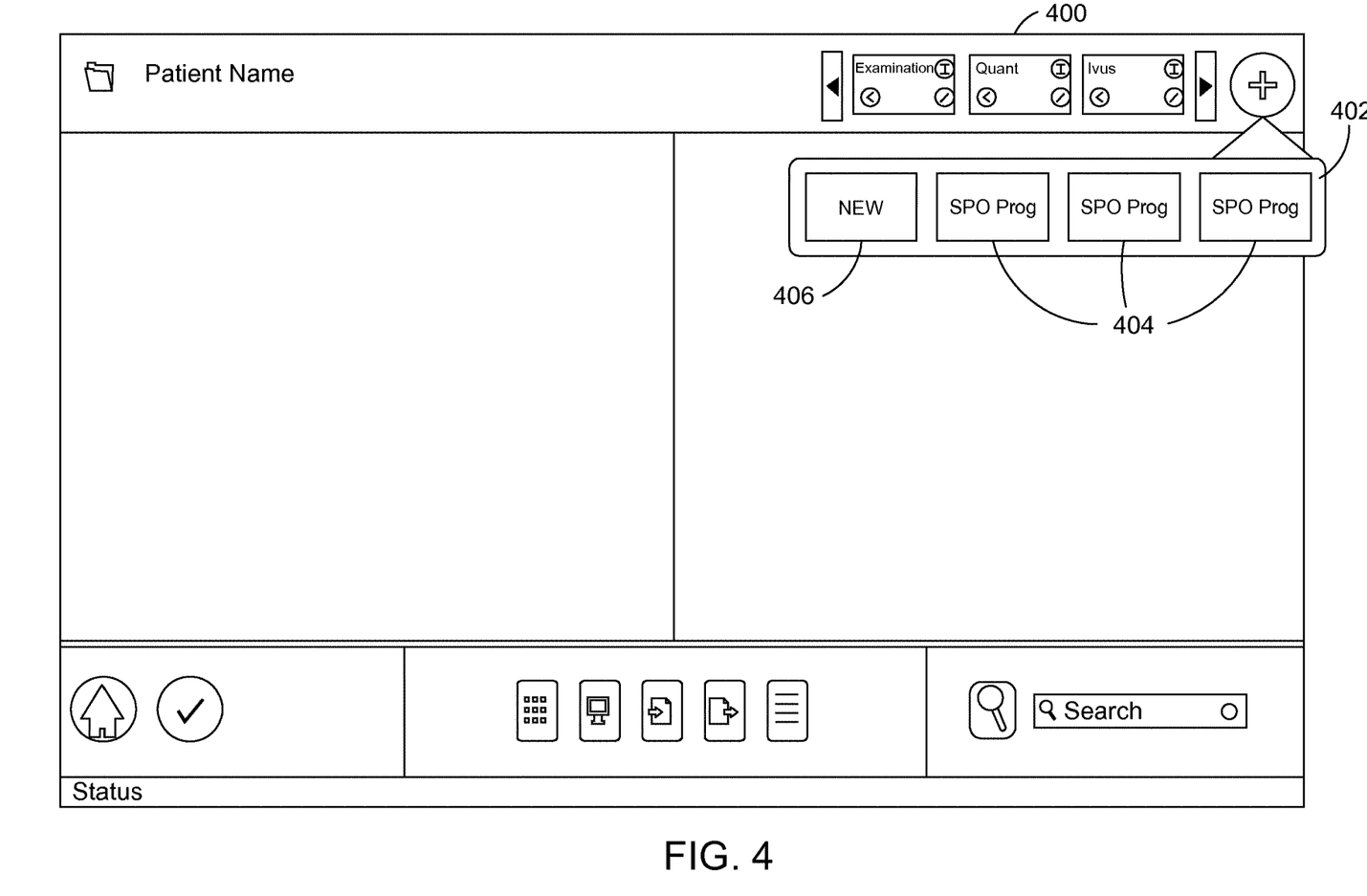
FIG. 4 is another exemplary screen shot showing an SPO program interface having a drop down menu according to embodiments described herein.

FIG. 3 shows an exemplary screen shot of a user interface (UI) 300 to interact with an SPO program according to embodiments disclosed herein. FIG. 4 shows another exemplary screen shot of a UI 400 to interact with an SPO program according to embodiments disclosed herein. The workflow processor 116 may interact with a user's computing device, such as physician's computing device 210, to provide the interface as shown in UI 300 at FIG. 3. The UI 300 and the UI 400 are examples of computer images presented to a user, such as a physician, for interface with one or more SPO programs that correspond to a particular patient.

As shown in FIG. 3, UI 300 may include a patient name area 302 that identifies a patient's name. In the embodiment shown in FIG. 3, the patient name area 302 is shown in the upper left hand corner of the screen. Embodiments may, however, include user interfaces having patient name areas at locations different from the location shown in FIG. 3. In some embodiments, a user may interact with the areas or portions of the UI 300 by moving a computer mouse or pressing keyboard keys to move about the portions of the display. The user may make selections (e.g., using a cursor and click a button on a mouse or pressing a key (such as "Enter") of a keyboard) to provide instructions to the workflow processor 116 executing or changing one or more SPOP programs. In other embodiments, the input device 114 may be a touch-based screen. A user may make selections by touching the screen at certain locations to provide input to the workflow processor 116 executing or changing one or more SPOP programs. The workflow processor 116 may provide any portion of data to support a physician planning for the procedure, which may include patient history (including data regarding earlier medical procedures), physical information (including patient height, weight, age, gender, etc.), patient allergy information, information pertaining to the examination location or room, and/or the type of requested procedure for the patient. Alternatively, the workflow processor 116 may provide data relevant to the physician presenting interfacing with the program or to a user (e.g., another physician) scheduled to conduct the medical procedure.

Referring again to FIG. 3, the UI 300 may include an area 304 (circle containing a plus sign image in FIG. 3) which may be used to create, update, or modify an SPO program for a patient. When a user (e.g., a physician) selects this area 304, the workflow processor 116 may be instructed to prompt a user to create, update, or modify the SPO program. For example, as shown in the UI 400 at FIG. 4, a drop-down menu 402 may be displayed when area 304 is selected (e.g., clicked) by the user. The physician can select one or more pre-existing SPO programs 404 to be modified from the introduced drop-down menu 402 or select a new SPO program 406 to be created. A user may then create one or more components of an SPO program for a particular patient, based on for example, the available medical information of the patient and for the medical procedure requested of the patient.

In some embodiments, the workflow processor 116 may automatically select a particular SPO program that a user may modify. The auto-selected program may be based on patient information, the type of medical procedure to be performed on the patient, and/or information pertaining to the physician scheduled to conduct the medical procedure on the patient. In some embodiments, the workflow processor 116 may auto-select SPO program parameters, such as tube voltage (kV), tube current (mA), initial C-arm position, fields of view and acquisition frame rates based on other parameters created or set by the physician. The workflow processor 116 may also list such parameters for consideration and selection by the physician. Some specific acquisition parameters may be tailored to the preferences of the individual physician performing the procedure as determined by the workflow processor 116 or selected by the physician. The workflow processor 116 may calculate injection dosage based on BMI or other patient information.

FIG. 5 is a system flow diagram illustrating workflow and interaction with the SPOP database 502. As shown at block 504 of FIG. 5, one or more portions of an SPOP may be constructed by the workflow processor 116 and/or a user, such as user 118 in FIG. 1, and the portions of the SPOP may be added to the patient profile, matched along with the patient information, and stored in the SPOP database 502. Upon the registration of a patient, such as patient 104 in FIG. 1, and determination by the user and/or workflow processor of programs and patient specific parameters to use for the medical procedure, the workflow processor 116 may register or store the SPOP in the SPOP database 502.

When the patient is in the examination room for the medical procedure, one or more registered or stored SPO programs may be made readily available for selection by the workflow processor. As shown at block 506 of FIG. 5, the patient may be prepared for examination in the examination room. A user, such as a physician or other person, in the examination room or control room may interact with a computer screen displaying, for example, the interface 300 shown in FIG. 3 as displayed by the workflow processor 116. An examination tab 306 of the interface 300 may be selected. The user may select the patient and/or physician through the UI 114. The user may request the workflow processor 116 to query the SPOP database 502 for specific programs based on the type of procedure to be performed for the specific patient. The patient may have previously been matched with one or more particular SPO programs that were created prior to the examination of the patient.

As shown at block 508 in FIG. 5, the SPOP database 502 may be queried by the workflow processor 116 for one or more additional SPO programs that may be used by the current physician for the current procedure and present these programs for user selection.

As shown in block 510 in FIG. 5, prior to or during the medical examination, one or more specifically requested SPO programs and/or one or more SPO programs auto-selected by workflow processor 116 may be displayed for selection in, for example, on one of the computing components shown in FIG. 2, such as SPOP server 202, examination room computer 204, hospital information infrastructure (HII) computer 206, control room computer 208 and physicians computer 210. The SPO programs may include acquisition parameters used in corresponding medical procedures. The operating physician may then select one or more displayed SPO programs, as presented by the workflow processor 116, which may for example command devices in the lab to move or provide instruction for an operator to move the device to a certain position. In some embodiments, SPO programs may execute to position the C-arm 108 to a predefined position and/or adjust the scanner 102 to acquire a needed image.

One or more SPO programs may be selected by the user 118 or automatically by the workflow processor 116 and subsequently executed by the workflow processor 116 or one or more other processors, such as processors in the examination or control room. The SPO program selections may be tracked by the workflow processor 116 and identified (e.g., labeled, displayed) by the workflow processor 116 or one or more other processors as one or more possible preferred programs in the SPOP database. In some embodiments, the identification as one or more possible preferred programs may occur for the current physician for the requested procedure and may be based on frequency of use.

As shown in block 512 in FIG. 5, the acquisition history, including information on type of image acquisition, for the particular physician may also be updated based on the acquisitions taken during the procedure and stored to the SPOP database 502. The SPOP database 502 may be used by the workflow processor 116 to suggest future parameters and one or more SPO programs for a particular physician for use in future procedures as more information (e.g. SPO programs) are stored in the SPOP database 502. In this manner, one or more preferred (e.g., most likely used) SPO programs may be made available (e.g., immediately) by the workflow processor 116 to the physician during the procedure or at the time one or more SPO programs are specifically requested. The one or more SPO programs may be specifically requested at the time of off-line patient setup by the physician.

System 200 shown in FIG. 2 may also support updates to pre-created SPO programs from multiple computing components, such as examination room computer 204, control room computer 208 and physician computer 210. New SPO programs can also be added if required for execution by the workflow processor 116 at any time.

Figure 6:
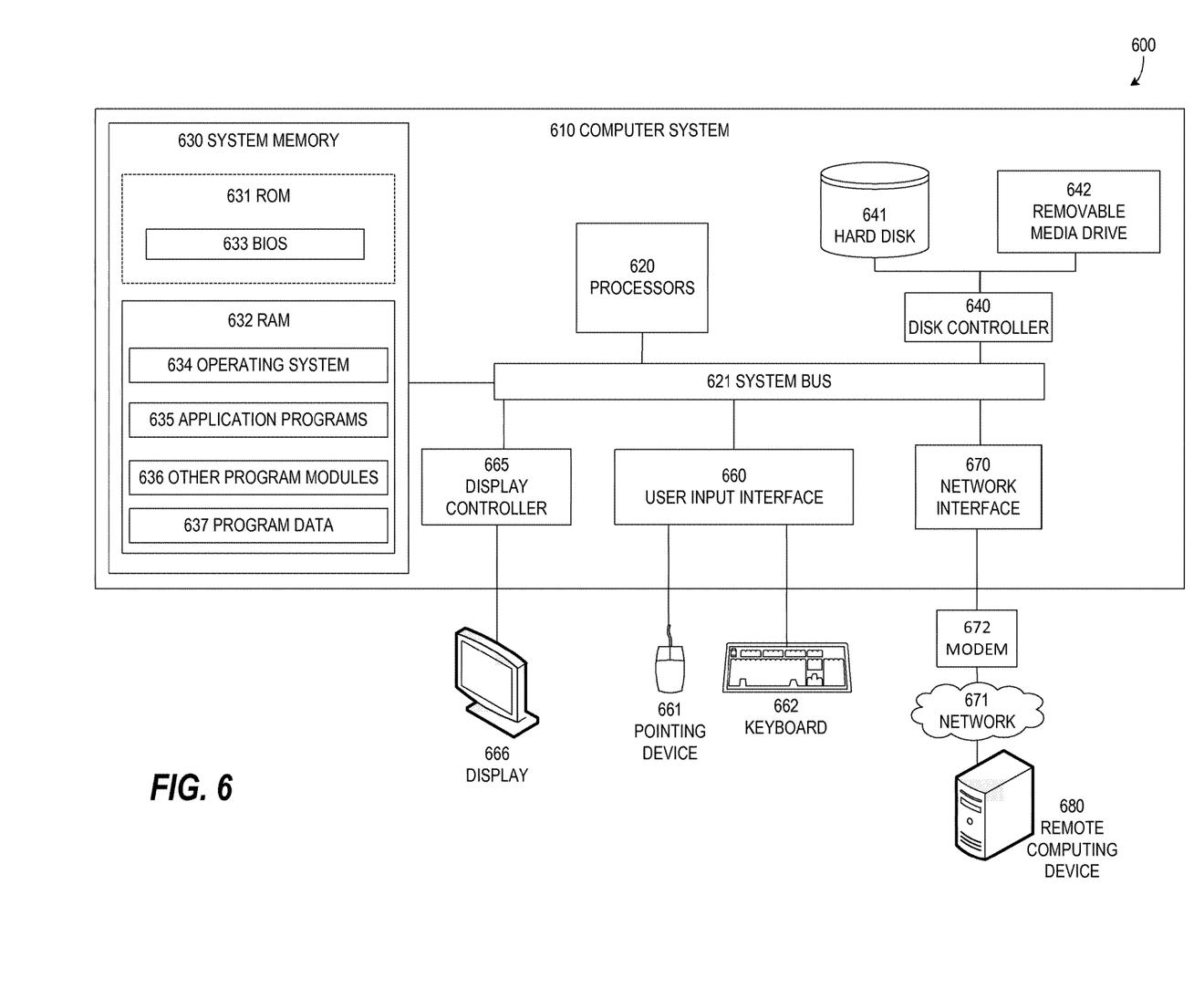
FIG. 6 illustrates an example of a computing environment within which embodiments of the invention may be implemented.

FIG. 6 illustrates an example of a computing environment 600 within which embodiments of the invention may be implemented. Computing environment 600 may be implemented as part of any component described herein. Computing environment 600 may include computer system 610, which is one example of a computing system upon which embodiments of the invention may be implemented. As shown in FIG. 6, the computer system 610 may include a communication mechanism such as a bus 621 or other communication mechanism for communicating information within the computer system 610. The system 610 further includes one or more processors 620 coupled with the bus 621 for processing the information. The processors 620 may include one or more CPUs, GPUs, or any other processor known in the art.

The computer system 610 also includes a system memory 630 coupled to the bus 621 for storing information and instructions to be executed by processors 620. The system memory 630 may include computer readable storage media in the form of volatile and/or nonvolatile memory, such as read only memory (ROM) 631 and/or random access memory (RAM) 632. The system memory RAM 632 may include other dynamic storage device(s) (e.g., dynamic RAM, static RAM, and synchronous DRAM). The system memory ROM 631 may include other static storage device(s) (e.g., programmable ROM, erasable PROM, and electrically erasable PROM). In addition, the system memory 630 may be used for storing temporary variables or other intermediate information during the execution of instructions by the processors 620. A basic input/output system 633 (BIOS) containing the basic routines that help to transfer information between elements within computer system 610, such as during start-up, may be stored in ROM 631. RAM 632 may contain data and/or program modules that are immediately accessible to and/or presently being operated on by the processors 620. System memory 630 may additionally include, for example, operating system 634, application programs 635, other program modules 636 and program data 637.

The computer system 610 also includes a disk controller 640 coupled to the bus 621 to control one or more storage devices for storing information and instructions, such as a magnetic hard disk 641 and a removable media drive 642 (e.g., floppy disk drive, compact disc drive, tape drive, and/or solid state drive). The storage devices may be added to the computer system 610 using an appropriate device interface (e.g., a small computer system interface (SCSI), integrated device electronics (IDE), Universal Serial Bus (USB), or FireWire).

The computer system 610 may also include a display controller 665 coupled to the bus 621 to control a display or monitor 666, such as a cathode ray tube (CRT) or liquid crystal display (LCD), for displaying information to a computer user. The computer system 610 includes a user input interface 660 and one or more input devices, such as a keyboard 662 and a pointing device 661, for interacting with a computer user and providing information to the processor 620. The pointing device 661, for example, may be a mouse, a trackball, or a pointing stick for communicating direction information and command selections to the processor 620 and for controlling cursor movement on the display 666. The display 666 may provide a touch screen interface which allows input to supplement or replace the communication of direction information and command selections by the pointing device 661.

The computer system 610 may perform a portion or all of the processing steps of embodiments of the invention in response to the processors 620 executing one or more sequences of one or more instructions contained in a memory, such as the system memory 630. Such instructions may be read into the system memory 630 from another computer readable medium, such as a hard disk 641 or a removable media drive 642. The hard disk 641 may contain one or more data stores and data files used by embodiments of the present invention. Data store contents and data files may be encrypted to improve security. The processors 620 may also be employed in a multi-processing arrangement to execute the one or more sequences of instructions contained in system memory 630. In alternative embodiments, hard-wired circuitry may be used in place of or in combination with software instructions. Thus, embodiments are not limited to any specific combination of hardware circuitry and software.

As stated above, the computer system 610 may include at least one computer readable medium or memory for holding instructions programmed according to embodiments of the invention and for containing data structures, tables, records, or other data described herein. The term "computer readable medium" as used herein refers to any non-transitory, tangible medium that participates in providing instructions to the processor 620 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 641 or removable media drive 642. Non-limiting examples of volatile media include dynamic memory, such as system memory 630. Non-limiting examples of transmission media include coaxial cables, copper wire, and fiber optics, including the wires that make up the bus 621. Transmission media may also take the form of acoustic or light waves, such as those generated during radio wave and infrared data communications.

The computing environment 600 may further include the computer system 610 operating in a networked environment using logical connections to one or more remote computers, such as remote computer 680. Remote computer 680 may be a personal computer (laptop or desktop), a mobile device, a server, a router, a network PC, a peer device or other common network node, and typically includes many or all of the elements described above relative to computer 610. When used in a networking environment, computer 610 may include modem 672 for establishing communications over a network 671, such as the Internet. Modem 672 may be connected to system bus 621 via network interface 670, or via another appropriate mechanism.

Network 671 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 610 and other computers (e.g., remote computing system 680). The network 671 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 671.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface (UI) comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

A workflow processor, as used herein, processes data to determine tasks to add to, or remove from, a task list or modifies tasks incorporated on, or for incorporation on, a task list, as for example specified in a program(s). A task list is a list of tasks for performance by a worker, user of a device, or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and may include an Event Monitor. A processor in the workflow engine tracks which processes are running, for which patients, physicians, and what step needs to be executed next, according to a process definition and may include a procedure for notifying physicians of a task to be performed.

The system and processes of the figures presented herein are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, the processes and applications may, in alternative embodiments, be located on one or more (e.g., distributed) processing devices on a network linking the units of FIG. 6. Any of the functions and steps provided in the Figures may be implemented in hardware, software or a combination of both. No claim element herein is to be construed under the provisions of 35 U.S.C. 112, sixth paragraph, unless the element is expressly recited using the phrase "means for."

Although the invention has been described with reference to exemplary embodiments, it is not limited thereto. Those skilled in the art will appreciate that numerous changes and modifications may be made to the preferred embodiments of the disclosure and that such changes and modifications may be made without departing from the true spirit of the disclosure. It is therefore intended that the appended claims covered be construed to all such equivalent variations as fall within the true spirit and scope of the disclosure.

The invention claimed is:

1. A medical workflow system comprising:
   at least one database configured to store one or more programs that are executable to operate a patient imaging device, patient data corresponding to one or more patients, medical procedure data corresponding to a type of patient medical procedure, and user data identifying a user to conduct a medical procedure using the medical procedure data;
   a workflow processor electrically connected to communicate with the at least one database and configured to determine which of the one or more programs to retrieve from the at least one database to provide to the user based on at least one of the patient data, the medical procedure data and the user data, wherein the workflow processor determines an additional one of the one or more programs to provide to the user that are likely to be used by a current physician for a current procedure, wherein the workflow processor automatically selects image acquisition parameters of at least one of the determined programs based on other parameters set by the current physician; and
   at least one user interface configured to provide a plurality of user selectable options comprising the determined programs by the workflow processor,
   wherein the workflow processor is further operative with a selected program that is selected from the provided programs to automatically position and control the patient imaging device for an image acquisition.

2. The system of claim 1 wherein the plurality of user selectable options comprise an option to modify the one or more programs and the processor is configured to modify the one or more programs in response to a selection to modify the one or more programs.

3. The system of claim 1 wherein the plurality of user selectable options comprise an option to create one or more new programs and the processor is configured to execute the one or more new programs in response to a selection to create the one or more new programs.

4. The system of claim 1, wherein the image acquisition parameters comprise at least one of a voltage of the patient imaging device or a current of the patient imaging device, or an angulation of a C-arm.

5. The system of claim 1 wherein the processor is further configured to update an acquisition history associated with the user based on the image acquisition and using the acquisition history to determine which of the one or more programs to provide to the user.

6. The system of claim 1 wherein the processor is further configured to match the one or more programs with the medical procedure data to determine which of the one or more programs to provide to the user.

7. The system of claim 1 wherein the processor is further configured to match the one or more programs with the user data to determine which of the one or more programs to provide to the user.

8. The system of claim 1 wherein the processor is configured to further determine which of the one or more programs to provide to the user based on frequency of use by the user.

9. A medical workflow method comprising:
storing one or more programs in a database that are executable to operate a patient imaging device;
storing, in the database, at least one of: i) patient data corresponding to one or more patients; (ii) medical procedure data corresponding to a type of patient medical procedure; and (iii) user data identifying a user to conduct a medical procedure using the medical procedure data;
managing, by a workflow processor, the at least one of: (i) the one or more programs; (ii) the patient data; (iii) the medical procedure data; and (iv) the user data stored in the database;
determining, by the workflow processor, which of the one or more programs to retrieve from the database to display to the user for user selection via a user interface based on at least one of the patient data, the medical procedure data and the user data determining an additional one of the one or more programs to provide to the user that are likely to be used by a current physician for a current procedure, and automatically selecting image acquisition parameters of at least one of the determined programs based on other parameters set by the current physician;
providing, via a user interface, a plurality of user selectable options comprising the determined programs; and
executing, by the workflow processor, a selected program selected from the provided programs to automatically position and control the patient imaging device for an image acquisition.

10. The method of claim 9 further comprising:
providing, via the user interface, an option to modify the one or more programs; and
modifying, by the workflow processor, the one or more programs in response to a selection to modify the one or more programs.

11. The method of claim 9 further comprising:
providing, via the user interface, an option to create one or more new programs; and
executing, by the workflow processor, the one or more new programs in response to a selection to create the one or more new programs.

12. The method of claim 9 further comprising matching, by the workflow processor, the one or more programs with the patient data to determine which of the one or more programs to provide to the user.

13. The method of claim 9 further comprising matching, by the workflow processor, the one or more programs with the medical procedure data to determine which of the one or more programs to provide to the user.

14. The method of claim 9, further comprising matching, by the workflow processor, the one or more programs with the user data to determine which of the one or more programs to provide to the user.

15. The method of claim 9, further comprising tracking, by the workflow processor, user selection of the one or more programs and labeling the one or more selected programs based on the frequency of use of the program by a user.

16. An article of manufacture for operating a workflow management system, the article of manufacture comprising a non-transitory, tangible computer-readable medium holding computer-executable instructions for performing a method comprising:
storing one or more programs in a database that are executable to operate a patient imaging device;
storing, in the database, at least one of: (i) patient data corresponding to one or more patients; (ii) medical procedure data corresponding to a type of patient medical procedure; and (iii) user data identifying a user to conduct a medical procedure using the medical procedure data;
managing, by a workflow processor, the at least one of: (i) the one or more programs; (ii) the patient data; (iii) the medical procedure data; and (iv) the user data stored in the database;
determining, by the workflow processor, which of the one or more programs to retrieve from the database to display to the user for user selection via a user interface based on at least one of the patient data, the medical procedure data and the user data determining an additional one of the one or more programs to provide to the user that are likely to be used by a current physician for a current procedure, and automatically selecting image acquisition parameters of at least one of the determined programs based on other parameters set by the current physician;
providing, via a user interface, a plurality of user selectable options comprising the determined programs; and
executing, by the workflow processor, a selected program selected from the provided programs to automatically position and control the patient imaging device for an image acquisition.

17. The article of manufacture of claim 16, further comprising instructions for:
providing, via the user interface, an option to modify the one or more programs; and
modifying, by the workflow processor, the one or more programs in response to a selection to modify the one or more programs.

18. The article of manufacture of claim 16, further comprising instructions for:
providing, via the user interface, an option to create one or more new programs; and executing, by the workflow processor, the one or more new programs in response to a selection to create the one or more new programs.

19. The method of claim 9 further comprising matching, by the workflow processor, the one or more programs with at least one of: (i) the patient data; (ii) the medical procedure data; and (iii) the user data to determine which of the one or more programs to provide to the user.

20. The system of claim 1 wherein the type of patient medical procedure is an interventional vascular X-ray treatment and the patient imaging device is an X-ray imaging device.

21. The system of claim 1 wherein the workflow processor is further configured to calculate injection dosage.

22. The system of claim 1 wherein the image acquisition parameters comprise at least one of a field of view and an acquisition frame rate of the patient imaging device.

* * * * *